United States Patent [19]

Shapiro

[11] Patent Number: 5,725,531

[45] Date of Patent: Mar. 10, 1998

[54] REAMING DEVICE

[76] Inventor: Jules S. Shapiro, 1725 W. Harrison #328, Chicago, Ill. 60612

[21] Appl. No.: 578,070

[22] Filed: Dec. 27, 1995

[51] Int. Cl.$^6$ ............................................. A61B 17/56
[52] U.S. Cl. ............................................................. 606/85
[58] Field of Search ............................ 606/85, 89, 80, 606/84, 81; 132/76.4, 76.5, 75.6, 75.3, 73.5; 433/142; 407/29.15, 29.13, 29.1

[56] References Cited

U.S. PATENT DOCUMENTS

| | | | |
|---|---|---|---|
| 2,019,580 | 11/1935 | Poux | 132/76.4 |
| 2,233,438 | 3/1941 | Troya | 132/76.4 |
| 4,587,964 | 5/1986 | Walker et al. | 606/85 |
| 4,872,452 | 10/1989 | Alexson . | |

OTHER PUBLICATIONS

Codman & Shurtlett, Inc. brochure entitled "General Surgical Instruments", pp. 174–175, Dec. 1973.
*Orthopedics*, Sep., 1990, pp. 1037–1044, Coughlin, Michael, vol. 13, No. 9.

*DePuy Catalog* page entitled, "Refine Fusion System". Author and date unknown.
*Zimmer Catalog* page entitled, "Modular Acetabular Reamers/Accessories" Author and date unknown.
*Zimmer Catalog* page entitled, "Modular Acetabular Reamers/Accessories" 1 page, no drawings except 1207–201. Author and date unknown.
Catalog page entitled, "Confield Total Shoulder System Instrumentation" p. E3, Author and date unknown.

*Primary Examiner*—Guy V. Tucker

[57] ABSTRACT

A device for preparing the ends of bones includes an elongated handle and at least one rasping head connected to the handle. The rasping head has first and second surfaces and rasping teeth which extend outwardly from the first surface. The ends of a pair of bones which form a joint are separated, and the rasping head is inserted between the end of the bones. One of the bones is forced against the second surface of the rasping head to force the rasping teeth against the end of the other bone, and the handle is moved back and forth through a limited arc to rotate the rasping teeth over the end of the other bone to prepare the end of the bone.

10 Claims, 4 Drawing Sheets

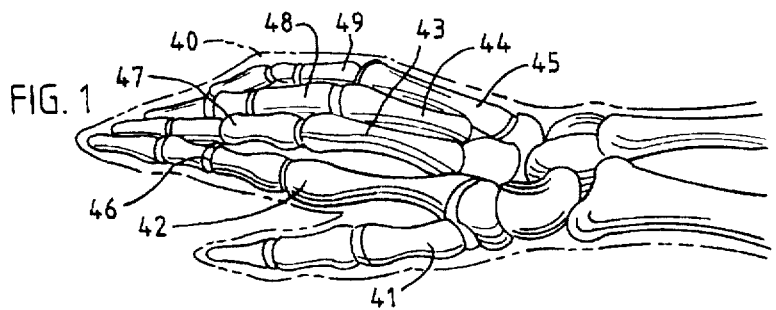
FIG. 1
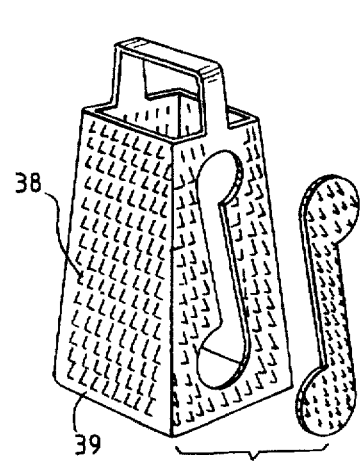
FIG. 2
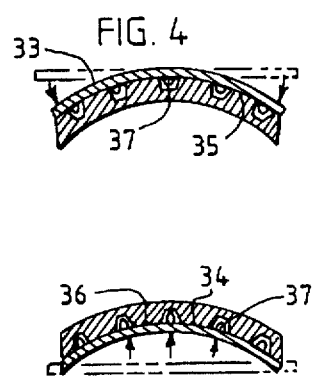
FIG. 4
FIG. 5
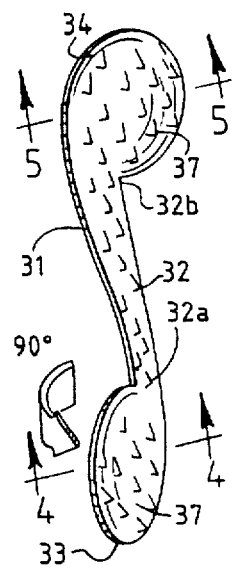
FIG. 3
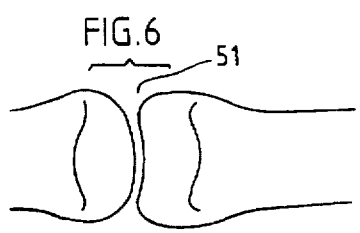
FIG. 6
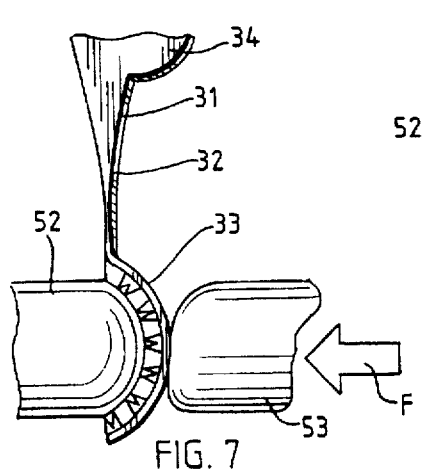
FIG. 7
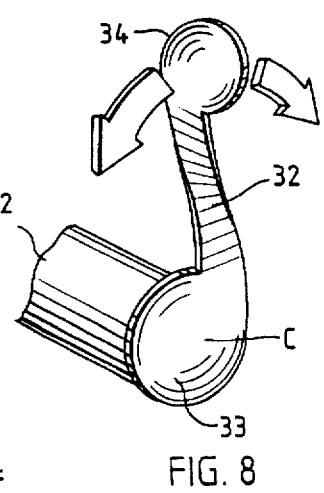
FIG. 8
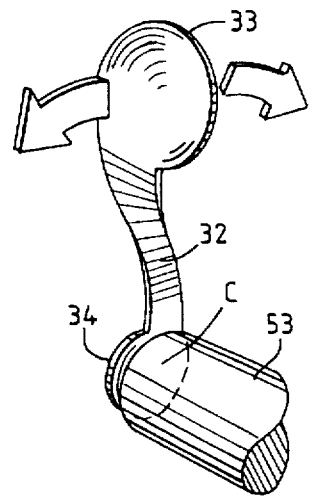
FIG. 9

5,725,531

1

REAMING DEVICE

BACKGROUND

This invention relates to a device and method for preparing the ends of bones (joints) so that they will fuse together more easily.

When preparing the ends of bones (joints) for fusion, orthopedic surgeons typically use devices called rasps or reamers. A rasp or reamer is frequently used for arthrodesis. Arthrodesis, the fusing together of two bones, is achieved by removing the cartilage and the articular surface on the ends of bones so that the raw cancellous (marrow type) bone of the ends can unite when such ends are held firmly together. The bone thus prepared is also occasionally used as the base into which a prosthesis (artificial joint) is placed.

For example, rasps or reamers are frequently used to prepare the metatarsophalangeal joints in the foot, the metacarpophalangeal joints in the hand, the proximal interphalangeal joint (PIP) in the hand, the carpometarcarpal joint (CMC) in the thumb, and the talonavicular joint in the foot. Rasps and reamers are also used for arthroplasties in which a bone is used as a base into which a prosthesis (artificial joint) is placed, such as in hip replacement surgery.

Currently and conventionally, such devices are used in line (parallel) with the bone, the force for reaming or rasping of the bone being applied centrally along a rod attached to the reamer or rasp, at 90 degrees to the reaming or rasping plate. This force is applied either by hand compression or with a powered drill type device. This necessitates opening the joint widely in order to apply such force, requiring extensive stripping of soft tissues and blood supply of the bones.

Another type of device is disclosed in U.S. Pat. No. 4,872,452. A bone rasp has a plate-like body having generally parallel surface portions and an attachment means for attaching the rasp to a source of oscillating-pivoting motion. The rasp has rasping portions arranged along the rasp to evenly rasp hard tissue. The rasping portion oscillates in an arc about the of motion C-1 in FIG. 1 of the patent.

SUMMARY OF THE INVENTION

The invention provides a rasp, reamer, or similar cutting or abrading device and a method for preparing the ends of bones for fusion. According to the invention, force is applied to the cutting device via a rod or handle which is attached at the periphery of the device, either radially or tangentially, but in the plane of the cutting surface, instead of at the center of the device, at 90 degrees to the cutting surface. The reamer or rasp is rotated through a limited arc in a clockwise and counterclockwise direction, preparing the bone ends without necessitating the extensive exposure of soft tissue which was previously required. Force is applied by pressing the opposing bone against the reamer or rasp and thence against the bone to be prepared. This results in limited stripping of soft tissues thereby reducing the risk of bone death, infection, and non-union of fusions.

In order to prepare the bones of a joint for fusion, the two bones of the joint are first slightly separated in a longitudinal direction. A first cutting device is inserted between the bones and onto the end of one of the bones. The handle is moved back and forth through a limited arc to rotate the cutting surface alternately clockwise and counterclockwise about the center of the cutting device while an axial force is exerted on the rasp device to force the cutting surface axially against the bone. The axial force is applied by pressing the

2 other bone of the joint against the opposite surface of the cutting device. A cutting device is then inserted on the end of the second bone of the joint, and the second bone is prepared in the same manner as the end of the first bone. In order to insure good fusion of the bones of the joint, the first cutting device may have a concave surface, and the second cutting device may have a convex surface.

DESCRIPTION OF THE DRAWINGS

The invention will be explained in conjunction with illustrative embodiments shown in the accompanying drawing, in which FIG. 1 is a fragmentary perspective view of the bones of the hand and wrist;

FIG. 2 is a perspective view of one embodiment of a bone rasp which is cut from a kitchen food grater;

FIG. 3 is an enlarged perspective view of the bone rasp of FIG. 2;

FIG. 4 is a sectional view taken along the line 4—4 of FIG. 3 showing a concave rasping surface;

FIG. 5 is a sectional view taken along the line 5—5 of FIG. 3 showing a convex rasping surface;

FIG. 6 is a fragmentary perspective view of the ends of two bones which form a joint in the hand or foot;

FIG. 7 is a side view of a bone rasp being used to prepare the end of a bone to have a convex surface;

FIG. 8 is a perspective view of the arc which the outer end of the bone rasp will subtend during the rasping of the end of a bone using a rasping head with a concave surface;

FIG. 9 is a perspective view of the arc which the outer end of the bone rasp will subtend during the rasping of the end of a bone using a rasping head with a convex surface;

DETAILED DESCRIPTION OF SPECIFIC EMBODIMENTS

Figure 10:
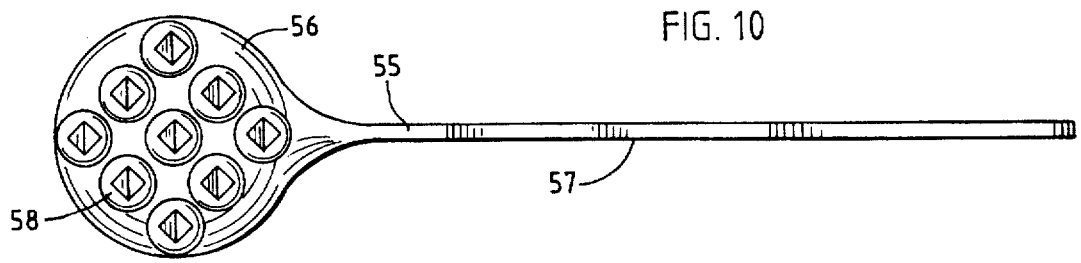
FIG. 10 is a plan view of another embodiment of a bone rasp having a rasping head with a convex surface attached radially to one end of an elongated handle.

Referring first to FIG. 3, the numeral 31 generally designates a bone rasp having an elongated handle 32 with first and second ends 32a and 32b. Rasping heads 33 and 34 are attached to the ends of the handle. The rasping head 33 has a concave rasping surface 35, and the head 34 has a convex rasping surface 36. Each of the rasping surfaces includes teeth 37 or similar rasping, reaming, cutting or abrading means for removing cartilage from the end of a bone to be prepared. The handle 32 is formed with a 90° twist so that the rasping surfaces of the heads 33 and 34 extend generally perpendicularly to each other.

The bone rasp 31 can be made from any suitable material, such as stainless steel. FIG. 2 illustrates how the bone rasp 31 can be formed by a cutting strip of metal from a typical kitchen food grater 38 having outwardly extending grating teeth 39. The concave and convex rasping heads 33 and 34 can be formed by deforming the ends of the strip as shown in FIG. 4 and 5.

Although the device illustrated in FIG. 3–5 is provided with rasping teeth, the invention is not limited to a conventional rasp or reamer. Any cutting or abrading device can be used which will remove cartilage from the ends of bone. For example, a radially oriented or star-shaped array of slots or some combination of sharp edges could be used.

The elongate handle 32 can also be a flat piece of metal, a rod, etc. The rasping heads 33 and 34 can be any shape, but are preferably round and connected radially or tangentially to the elongate handle 32. Although the rasping surfaces of the heads 33 and 34 are concave and convex, respectively, the rasping surfaces could have some other shape or could be flat.

FIG. 1 illustrates the bones of a hand 40. The hand includes metacarpals 41–45 and phalanges 46–50. FIG. 6 is an enlarged view of one of the metacarpophalangeal joints 51 which is to be prepared for fusion. After the joint is exposed, the ends of the bones are separated slightly, and one of the heads of the rasp 31 is inserted between the bone ends as shown in FIG. 7. In the example illustrated in FIG. 7, the head 33 with the concave rasping surface is applied against the end of metacarpal 52. The rasping head 33 is rotated alternately clockwise and counterclockwise about the center C of the rasping surface as illustrated in FIG. 8 while phalange 53 is pressed axially or longitudinally against the rasping head as indicated by the arrow F. The axial force applied to the rasping head by the phalange forces the concave rasping surface against the end of the metacarpal as the rasping surface rotates. The rasping surface thereby removes the cartilage from the end of the metacarpal and forms a convex surface of cancellous bone.

The rasping surface is rotated by grasping the handle 32 or outer rasping head 34 and rotating the handle through an arc of about 60° as shown in FIG. 8. The surface of the head 34 extends generally perpendicularly to the surface of the head 33 and facilitates applying a rotational force which lies generally in the plane of the head 33 and which is perpendicular to the axis of the bone. Although the rasping surfaces are curved and not planar, the plane of the surface can be defined by the plane in which the outer edge of the surface lies. The surgeon can easily rotate the rasp with one hand while forcing the phalange 53 against the rasping head with the other hand.

The surface of the rasping head which is opposite the rasping surface does not have teeth and is smooth except for the openings which form the teeth on the rasping surface. The phalange can therefore be pressed against the non-rasping surface of the rasping head without being abraded.

FIG. 9 illustrates the end of the phalange 53 being prepared by the convex rasping head 34 to form a concave surface of cancellous bone on the end of the phalange. The rasping head 34 is rotated about its center C while being forced against the end of the phalange by pressing the metacarpal longitudinally against the rasping head.

Figure 22:
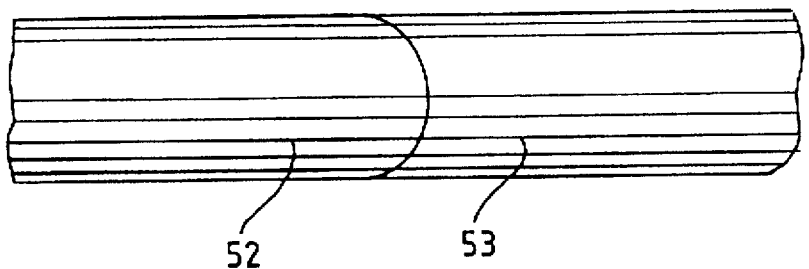
FIG. 22 is a perspective view of the prepared concave and convex ends of bones which have been coapted and fused.
Figure 23:
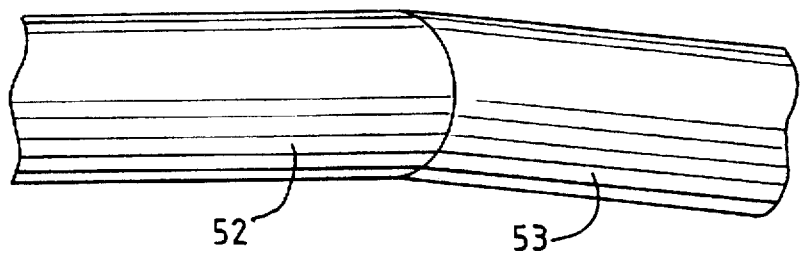
FIG. 23 is a view similar to FIG. 22 in which the bones are slightly out of axial alignment.

FIG. 22 illustrates the prepared ends of the metacarpal and phalange coapted so that the raw cancellous surfaces can fuse together. The mating or nesting concave and convex surfaces of the bone ends provide greater surface area contact than flat ends and allow for changes in the position of fusion without loss of contact area. For example, FIG. 23 illustrates a bone joint which has been fused with the bones slightly out of longitudinal alignment.

The handle 32 acts as a lever arm for rotating the rasping head. Rotating the handle alternately in opposite directions about the center of the rasping head will cause the rasping surface to rotate in opposite directions about its center. By moving the bone rasp in such a manner, the end of the bone is prepared without extensively exposing the bone. This results in limited stripping of soft tissues which reduces the risk of bone death, infection, and non-union.

Figure 11:
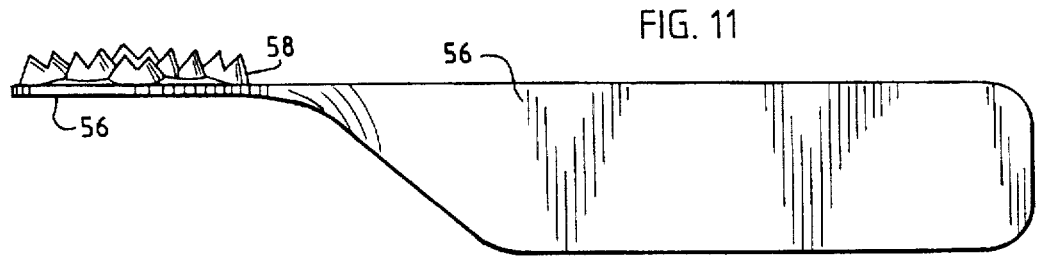
FIG. 11 is a side view of the bone rasp of FIG. 10.

A modified embodiment of a bone rasp 55 is illustrated in FIGS. 10 and 11. A single rasping head 56 having a convex rasping surface is radially attached to an elongated handle 57. The plane of the handle is generally perpendicular to the rasping head for applying a rotating force to the rasping head which lies generally in the plane of the head. Teeth 58 are formed by punching the metal of the head like teeth of a food grater.

Figure 12:
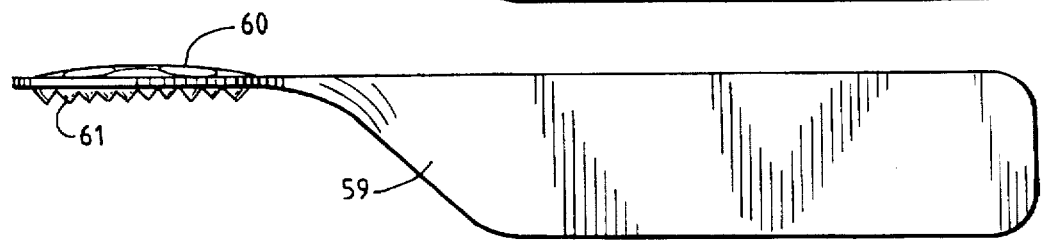
FIG. 12 is a side view of a bone rasp similar to the rasp of FIGS. 10 and 11 but having a concave rasping surface.

FIG. 12 shows a bone rasp 49 which is similar to the rasp 55, but rasping head 60 has a concave rasping surface with teeth 61.

Figure 13:
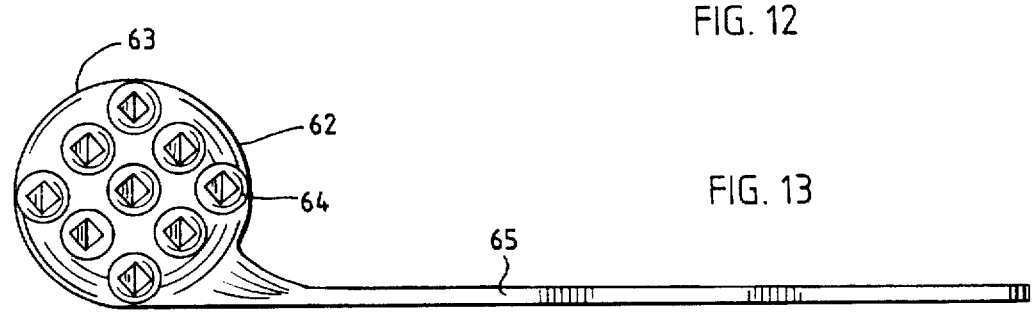
FIG. 13 is a plan view of another embodiment of a bone rasp having a rasping head with a convex surface attached tangentially to one end of the elongate handle.
Figure 14:
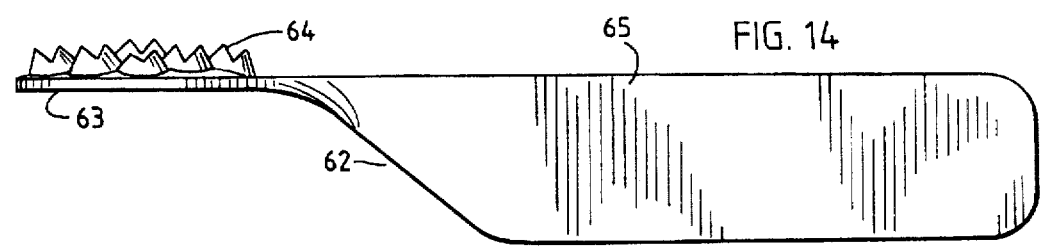
FIG. 14 is a side view of the bone rasp of FIG. 13.

Another embodiment of a bone rasp 62 is shown in FIGS. 13 and 14. A single rasping head 63 having a convex rasping surface with rasping teeth 64 is tangentially attached to one end of an elongated handle 65.

Figure 15:
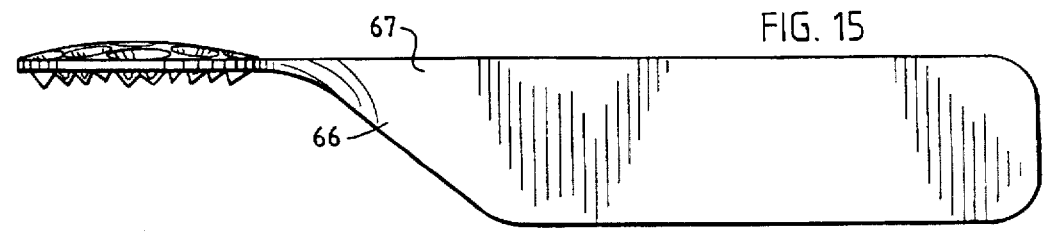
FIG. 15 is a side views of a bone rasp similar to the rasp of FIGS. 13 and 14 but having a concave surface.

FIG. 15 illustrates a similar rasp 66 having a concave rasping surface which is tangentially attached to a handle 67.

Figure 16:
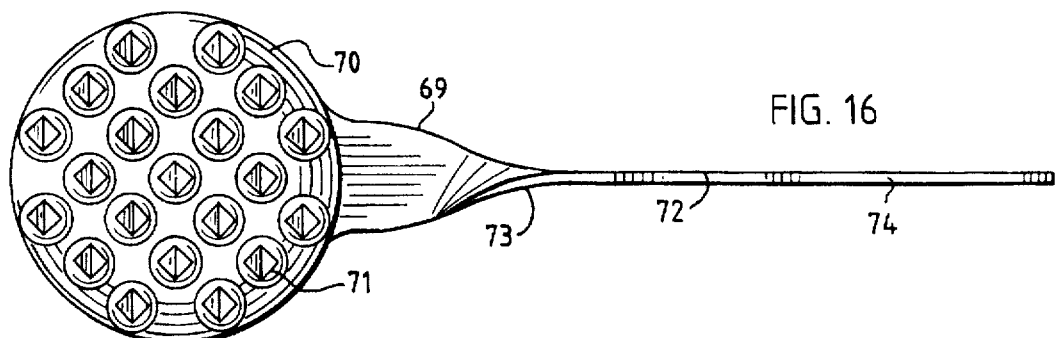
FIG. 16 is a plane view of yet another embodiment of the bone rasp having more rasping teeth and a helically twisted handle.
Figure 17:
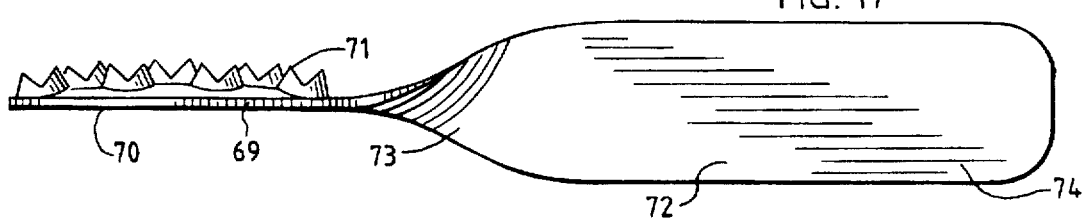
FIG. 17 is a side view of the bone rasp of FIG. 16.

Still another embodiment of a bone rasp 69 is illustrated in FIGS. 16 and 17. The bone rasp 69 includes a rasping head 70 having a convex rasping surface with teeth 71 and a handle 72. The handle extends radially from the rasping head and is provided with a 90° twist 73 so that the end portion 74 lies in a plane which is perpendicular to the plane of the rasping surface.

Figure 18:
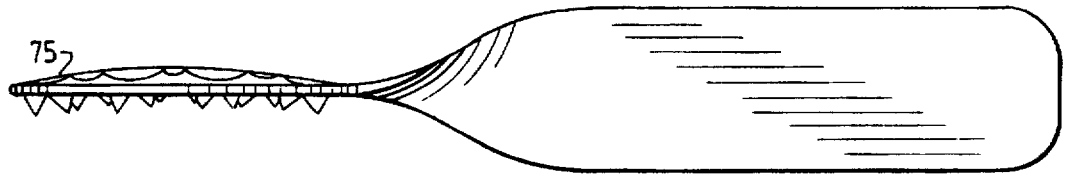
FIG. 18 is a side view of a bone rasp similar to the rasp of FIGS. 16 and 17 but having a concave surface.

FIG. 18 illustrates a similar rasp 75 with a concave rasping surface.

Figure 19:
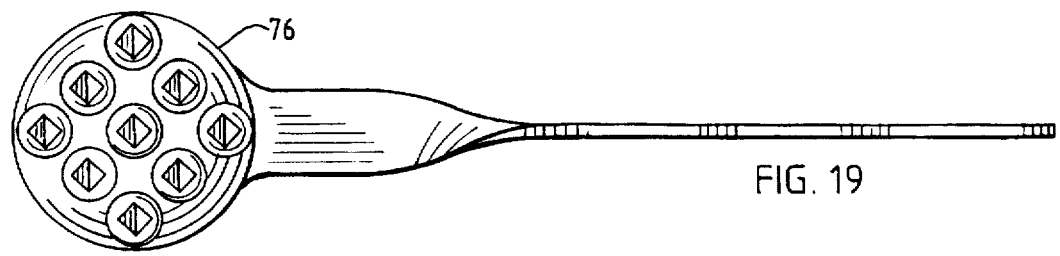
FIG. 19 is a plan view of a bone rasp which is similar to the rasp of FIG. 16 but which has fewer rasping teeth.
Figure 20:
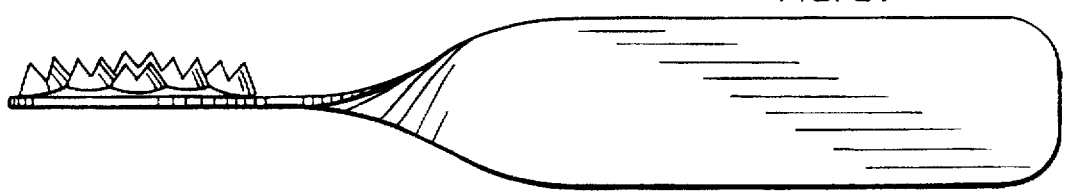
FIG. 20 is a side view of the bone rasp of FIG. 19.
Figure 21:
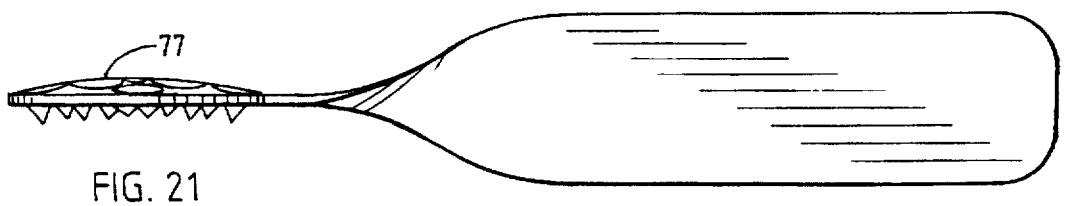
FIG. 21 is a side view of a bone rasp similar to the rasp of FIGS. 19 and 20 but having a concave surface.

FIGS. 19–21 illustrate rasps 76 and 77 which are similar to rasps 69 and 75, respectively, but have fewer rasping teeth.

The rasps can be used to prepare the bones of any joint in the hand or foot which are commonly prepared for fusion by rasps or reamers. The rasps can also be used in arthroplasties in which a bone is prepared to receive a prosthesis.

While in the foregoing specification a detailed description of a specific embodiment of the invention was set forth for the purpose of illustration, it will be understood that many of the details herein given may be varied considerably by those skilled in the art without departing from the spirit and scope of the invention.

I claim:

1. A device for removing cartilage from the end of a bone comprising:
   an elongated handle having first and second ends;
   a first rasping head connected to the first end of the elongated handle and having a concave rasping surface and means for removing cartilage on the rasping surface;

a second rasping head connected to the second end of the elongated handle and having a convex rasping surface and means for removing cartilage on the rasping surface, the concave and convex surfaces having substantially mating contours whereby a bone end prepared by the concave rasping surface can mate with a bone end prepared by the convex rasping surface.

2. The device of claim 1 wherein the handle extends radially from the first and second rasping head.

3. The device of claim 1 wherein the handle extends tangentially from the first and second rasping heads.

4. The device of claim 1 in which each of the rasping heads includes a generally circular outer periphery.

5. The device of claim 4 in which the circular outer periphery of each rasping head defines a plane of the rasping head, the planes of the two rasping heads extending generally perpendicularly.

6. The device of claim 4 in which each of the rasping heads includes a substantially smooth surface opposite the rasping surface.

7. A device for removing cartilage from the end of a bone comprising:

an elongated handle having first and second ends;

a first rasping head connected to the first end of the elongated handle and having a concave rasping surface and means for removing cartilage on the rasping surface;

a second rasping head connected to the second end of the elongated handle and having a convex rasping surface and means for removing cartilage on the rasping surface, the elongated handle having a longitudinal axis and being helically twisted about the longitudinal axis.

8. The device of claim 7 wherein the elongated handle is helically twisted about 90°.

9. The device of claim 7 in which each of the rasping heads includes a generally circular outer periphery and in which the circular outer periphery of each rasping head defines a plane of the rasping head, the planes of the two rasping heads extending generally perpendicularly.

10. The device of claim 7 in which each of the rasping heads includes a substantially smooth surface opposite the rasping surface.

* * * * *